United States Patent
Fritz et al.

(10) Patent No.: US 9,630,866 B2
(45) Date of Patent: *Apr. 25, 2017

(54) PROCESS FOR WORKUP OF $NO_x$-CONTAINING OFFGASES FROM WASTEWATER STREAMS OF NITRATION PLANTS

(75) Inventors: Ruediger Fritz, Bernsdorf (DE); Renate Hempel, Ruhland (DE); Michael Zoellinger, Eislingen (DE); Holger Allardt, Schwarzheide (DE); Reiner Reetz, Schwarzheide (DE)

(73) Assignee: BASF SE, Ludwigshafen (DE)

( * ) Notice: Subject to any disclaimer, the term of this patent is extended or adjusted under 35 U.S.C. 154(b) by 550 days.

This patent is subject to a terminal disclaimer.

(21) Appl. No.: 13/511,256

(22) PCT Filed: Dec. 13, 2010

(86) PCT No.: PCT/EP2010/069530
§ 371 (c)(1),
(2), (4) Date: May 22, 2012

(87) PCT Pub. No.: WO2011/082977
PCT Pub. Date: Jul. 14, 2011

(65) Prior Publication Data
US 2012/0228218 A1   Sep. 13, 2012

(30) Foreign Application Priority Data

Dec. 16, 2009 (EP) .................................. 09179507

(51) Int. Cl.
| | | |
|---|---|---|
| C02F 1/66 | (2006.01) |
| C02F 9/00 | (2006.01) |
| C01B 21/40 | (2006.01) |
| C07C 201/08 | (2006.01) |
| C02F 1/20 | (2006.01) |
| C02F 1/78 | (2006.01) |
| C02F 103/36 | (2006.01) |

(52) U.S. Cl.
CPC ................ *C02F 9/00* (2013.01); *C01B 21/40* (2013.01); *C07C 201/08* (2013.01); *C02F 1/20* (2013.01); *C02F 1/78* (2013.01); *C02F 2103/36* (2013.01); *C02F 2209/008* (2013.01); *C02F 2209/02* (2013.01); *C02F 2209/06* (2013.01)

(58) Field of Classification Search
CPC ........... C02F 1/66; C02F 1/26; C02F 2103/36
USPC ...... 210/665, 612, 631, 749; 435/262, 262.5
See application file for complete search history.

(56) References Cited

U.S. PATENT DOCUMENTS

| | | | |
|---|---|---|---|
| 4,230,567 A | 10/1980 | Larbig | |
| 4,642,396 A * | 2/1987 | Carr et al. | 568/934 |
| 4,755,499 A * | 7/1988 | Neal et al. | 502/415 |
| 4,772,757 A * | 9/1988 | Lailach et al. | 568/939 |
| 6,245,242 B1 | 6/2001 | Schuster et al. | |
| 6,506,948 B1 | 1/2003 | Sawicki | |
| 6,936,741 B2 * | 8/2005 | Munnig et al. | 568/934 |
| 2002/0033366 A1 | 3/2002 | Pasquale et al. | |
| 2004/0267062 A1 | 12/2004 | Munnig et al. | |
| 2007/0043244 A1 | 2/2007 | Buettner | |

FOREIGN PATENT DOCUMENTS

| | | |
|---|---|---|
| DE | 101 43 800 | 8/2002 |
| EP | 0 005 203 | 11/1979 |
| EP | 0 953 546 | 11/1999 |
| EP | 1 178 017 | 2/2002 |
| EP | 1 493 730 | 1/2005 |
| JP | 48-33655 | 5/1973 |
| WO | 2005 037766 | 4/2005 |
| WO | 2009 027416 | 3/2009 |

OTHER PUBLICATIONS

Japanese Office Action issued Jan. 21, 2014 in Patent Application No. 543660/2012 (English Translation only).
Kirk-Othmer, "Nickel and nickel alloys to paint," Encyclopedia of chemical technology, 4$^{th}$ edition, vol. 17, pp. 133-152, (1996).
"Ullmanns Enzyklopedie der technischen Chemie," 4$^{th}$ edition, vol. 17, pp. 386-387, (1979).
Holleman-Wiberg, "Lehrbuch der Anorganischen Chemie," 101$^{st}$ edition, pp. 690-710, (1995).
International Search Report Issued Jun. 28, 2011 in PCT/EP10/69530 Filed Dec. 13, 2010.
U.S. Appl. No. 13/514,648, filed Jun. 8, 2012, Fritz, et al.
U.S. Appl. No. 13/516,280, filed Jun. 15, 2012, Fritz, et al.

* cited by examiner

*Primary Examiner* — Nam Nguyen
*Assistant Examiner* — Claire Norris
(74) *Attorney, Agent, or Firm* — Oblon, McClelland, Maier & Neustadt, L.L.P.

(57) ABSTRACT

The present invention relates to a process for workup of nitrite-comprising alkaline process wastewaters from the nitration of aromatic compounds, wherein the alkaline process wastewater is acidified by addition of acids and the offgas which comprises nitrogen oxides and escapes from the acidified process wastewater is worked up, comprising the steps of
 a) acidifying the process wastewater by adding acid to a pH below 5, which forms an organic phase which separates out, an acidic aqueous phase and a gaseous $NO_x$-containing phase, and
 b) removing the gaseous $NO_x$-containing phase.

17 Claims, No Drawings

PROCESS FOR WORKUP OF NO$_x$-CONTAINING OFFGASES FROM WASTEWATER STREAMS OF NITRATION PLANTS

The present invention relates to a process for workup of nitrite-comprising alkaline process wastewaters from the nitration of aromatic compounds, wherein the alkaline process wastewater is acidified by addition of acids and the offgas which comprises nitrogen oxides and escapes from the acidified process wastewater is worked up.

Aromatic nitro compounds such as mono- and dinitrotoluene are typically prepared by nitrating the corresponding aromatic compounds by means of a mixture of concentrated nitric acid and concentrated sulfuric acid, which is referred to as nitrating acid. This forms an organic phase which comprises the crude product of the nitration, and an aqueous phase which comprises essentially sulfuric acid, water of reaction and water introduced by the nitrating acid. The nitric acid is consumed almost completely in the nitration.

After separation of the two phases, the aqueous, sulfuric acid-containing phase, according to the technology of the nitrating process, is mixed again with fresh nitric acid, directly or after concentration, and used for nitration. However, at least some of the sulfuric acid must be discharged continuously or batchwise from the overall process in order to avoid concentration of impurities, especially of metallic salts (see also DE 10 143 800 C1). The impurities are, for example, impurities originally present in the nitric acid, and metal compounds which are leached out of the reactor and pipe materials under the highly corrosive conditions which exist in the course of reaction and workup of the aqueous phase.

In the concentration of the aqueous, sulfuric acid-containing phase obtained in the nitration, an aqueous distillate with low sulfuric acid content, referred to hereinafter as aqueous distillate of the sulfuric acid concentration, and a phase with a high sulfuric acid content, referred to hereinafter as concentrated sulfuric acid, are obtained. The portion of the concentrated sulfuric acid discharged from the nitrating process is also referred to hereinafter as waste sulfuric acid.

The crude product of the nitration of aromatic compounds, such as benzene, toluene, xylene, chlorobenzene, etc, to the corresponding nitroaromatics typically comprises, as well as the desired nitroaromatics such as nitrobenzene (NB) and dinitrobenzene (DNB), mono- and dinitrotoluene (MNT and DNT), nitrochlorobenzene (NCB) or nitroxylene, also small amounts of mono-, di- and trinitrophenols (referred to hereinafter as nitrophenols), mono-, di- and trinitrocresols (referred to hereinafter as nitrocresols) and mono-, di- and trinitroxylenols (referred to hereinafter as nitroxylenols) and other compounds comprising hydroxyl groups and nitro groups, and also mono- and dinitrobenzoic acids (referred to hereinafter as nitrobenzoic acids).

Aromatic nitro compounds which do not comprise a hydroxyl group or carboxyl group in the molecule are also referred to in the context of the invention as neutral nitro species or neutral nitroaromatics. Nitrophenols, nitrocresols, nitroxylenols and nitrobenzoic acids are also summarized hereinafter as hydroxynitroaromatics.

The crude product from the nitration has to be freed from the undesired by-products before further use. Typically, the by-products, after removal of the nitrating acid, are removed by multistage scrubbing with acidic, alkaline and neutral scrubbing liquid, generally in the sequence stated. The alkaline scrubbing is typically performed with aqueous sodium hydroxide solution, aqueous sodium carbonate solution or aqueous ammonia solution. The alkaline process wastewater which arises comprises nitrophenols, nitrocresols, nitroxylenols and nitrobenzoic acids, in the form of their water-soluble salts of the base used. They are typically present in a concentration of 0.2 to 2.5% by weight, based on the alkaline process wastewater. The alkaline process wastewater also comprises neutral nitro species formed in the nitration, especially reaction products. Neutral nitro species are present in the alkaline process wastewater, typically in an amount of several 1000s of ppm. The alkaline process wastewater generally comprises 500 to 5000 ppm of nitrates, 500 to 5000 ppm of nitrite and several hundred ppm of sulfate. These ions originate from the nitration. The ingredients give rise to a chemical oxygen demand of 1000 to 20 000 mg/l.

The nitrophenols, nitrocresols, nitroxylenols, nitrobenzoic acids and in particular the salts thereof are intensely colored and highly toxic to the environment. Moreover, the nitrophenols and especially their salts, in relatively high concentrations or in substance, are explosives and have to be removed from the wastewater before the release thereof and disposed of in such a way that no risk to the environment emanates from them. The alkaline process wastewater also comprises neutral nitro species formed in the nitration, especially reaction products. Since the aromatic nitro compounds have bactericidal properties overall and hence make biological purification of the wastewater impossible, purification or workup of the wastewater comprising aromatic nitro compounds is necessary.

Numerous processes for removal of the nitrophenols, nitrocresols, nitroxylenols, nitrobenzoic acids and the neutral nitroaromatics from the process wastewaters are described in the literature, for example extraction, adsorption, oxidation or thermolysis.

The Encyclopedia of Chemical Technology, Kirk-Othmer, Fourth Edition 1996, Vol. 17, p. 138 describes an extraction process for removing nitrobenzene, in which the nitrobenzene dissolved in the wastewater at the appropriate temperature is removed by extraction with benzene. Benzene which has dissolved in the water is removed by stripping before the final treatment of the wastewater.

According to U.S. Pat. No. 6,506,948, the wash phases obtained in the nitration of toluene are extracted directly with toluene, each of the wastewater streams which arise being extracted separately. The toluene stream is subsequently conducted into the nitration process and converted. This leaves nitrocresols and nitrobenzoic acids dissolved in the alkaline wastewater stream, which subsequently have to be removed separately.

EP 0 005 203 describes a thermal process for workup of wastewaters comprising hydroxynitroaromatics. In this case, the wastewaters which comprise the hydroxynitroaromatics in the form of water-soluble salts thereof are heated with exclusion of air and oxygen under pressure to temperatures in the range of 150 to 500° C.

EP 0 953 546 discloses a thermal process for workup of wastewater streams from nitration plants, in which hydroxynitroaromatics and neutral nitroaromatics can be degraded at the same time.

According to WO 2009/027416 A1, prior to the thermolytic treatment of the alkaline wastewaters from the nitration, the aromatic nitro compounds which do not comprise any hydroxyl groups and are dissolved therein are removed by extraction.

The dissolved nitroaromatics and hydroxynitroaromatics can additionally be removed in an acidic medium by extraction with an organic solvent (Ullmanns Enzyklopädie der technischen Chemie, 4th edition, Volume 17, page 386).

The hydroxynitroaromatics present in the alkaline process wastewater can also be transferred by acidification to an organic phase which separates out and is subsequently removed. In order to prevent the crystallization of the hydroxynitroaromatics, the apparatus used for the separation and removal has to be heated. Nevertheless, the problem of "fouling" occurs. This means that the pumps and pipe systems used to remove the organic phase which separates out become blocked very rapidly by precipitating and crystallizing impurities, and there is therefore a high requirement for cleaning.

Such a process is described in EP 1 493 730 A1. In this process, the wastewater streams of the acidic and alkaline DNT scrubbings and from the sulfuric acid concentration are mixed, such that a pH below 5 is established. The wastewater from the sulfuric acid concentration is the distillate of the sulfuric acid concentration with a sulfuric acid concentration of 0.2 to 1% by weight. In the course of acidification, an organic phase separates out, which is removed. The aqueous phase is supplied separately to a further wastewater treatment.

In addition, it is known that, in dinitrotoluene preparation, the dinitrotoluene-containing alkaline wastewater can be freed from the major portion of the 2,4- and 2,6-dinitrotoluene dissolved at 70° C. by an absorption on sewage sludge, before the hydroxynitroaromatics are digested by means of ozonization. The problem occurs here that the nitrocresols cannot be converted by the ozonization. In addition, the alkaline wastewater still comprises nitrite, which is only oxidized by ozone to nitrate and thus leads to an increased ozone demand. For instance, at a concentration of 3000 mg/l of nitrite in the alkaline process wastewater, about 25 to 40% of the ozone is consumed for the nitrite oxidation.

It is therefore an object of the present invention to provide a process for workup of alkaline process wastewaters from the nitration of aromatic compounds, in which by-products and waste products obtained in the nitration of aromatic compounds can be reutilized in the process and/or can be cited to the other further processes for wastewater disposal or workup with a low loading of unwanted constituents.

This object is achieved by the following process for workup of alkaline process wastewaters from the nitration of aromatic compounds to mono-, di- and trinitroaromatics, comprising the steps of
a) acidifying the process wastewater by adding acid to a pH below 5, which forms an organic phase which separates out, an acidic aqueous phase and a gaseous $NO_x$-containing phase, and
b) removing the gaseous $NO_x$-containing phase.

On acidification of the alkaline process wastewater, the nitrites present therein give rise to nitrous acid, which is unstable under the acidic conditions and decomposes to NO, $NO_2$ and nitric acid. The nitrogen oxides formed, NO and $NO_2$, can, as described in "Lehrbuch der Anorganischen Chemie" [Inorganic Chemistry], Holleman-Wiberg, 101st edition 1995, pp. 690-710, for example, react further to give higher gaseous nitrogen oxides such as $N_2O_3$ and $N_2O_4$, or with dimerization to give $N_2O_2$. The nitrogen oxides and the higher homologs thereof are referred to hereinafter as $NO_x$.

The alkaline process wastewater treated by the process according to the invention has a much lower nitrite concentration. This facilitates the further workup of the aqueous phase.

Typically, the percentage lowering of the nitrite content in an alkaline process wastewater treated in accordance with the invention from a plant for preparation of dinitrotoluene totals 90-99% (nitrite).

The organic phase which separates out comprises the majority of the neutral nitroaromatics and hydroxynitroaromatics present in the alkaline process wastewater; the acidic aqueous phase is highly depleted of these compounds.

The $NO_x$-containing offgas can then be disposed of in different ways, for example by combustion with downstream catalysts for offgas cleaning or by alkaline absorption of the offgas stream formed from the acidification, for example with NaOH or other alkaline scrubbers. In the case of alkaline absorption, it is particularly disadvantageous that $CO_2$, which may likewise be present in the offgas stream, is likewise absorbed and increases the amount of alkali required.

In a preferred embodiment, the $NO_x$ present in the phase removed is sent back to the nitric acid preparation. An exceptional saving of raw material is achieved when the nitric acid thus obtained is used again in the nitration of the aromatic compounds, since the $NO_x$ in this way is not lost to the nitration process.

In a further preferred embodiment of the process according to the invention, the sulfuric acid from the preparation process for the nitroaromatics, which is obtained in the concentration step, is used for the acidification of the alkaline process wastewater. This is especially advantageous since a proportion of the concentrated sulfuric acid must in any case be discharged from the circuit of nitration and sulfuric acid workup and disposed of as what is called waste sulfuric acid. The concentrated sulfuric acid comprises the salts obtained as a result of corrosion (pipelines) in the course of nitration, comprising Fe, Cr, Ni, Ta and traces of further heavy metals in the form of their sulfates. Typically, in the case of a rise in the salt concentration above 300 ppm, some of the acid has to be discharged from the process as so-called waste sulfuric acid and has to be disposed of or purified by other processes. The use of this waste sulfuric acid is therefore particularly advantageous. It has been found that, surprisingly, a substream of the amount of concentrated sulfuric acid to be discharged can be used in the process according to the invention, without any further addition of additional acid being required. This leads to very economic use of the different streams.

The process according to the invention is used for workup of alkaline process wastewater from the nitration of aromatic compounds. Preference is given to using the process in the nitration of benzene, toluene, xylene, chlorobenzene and/or dichlorobenzene.

The alkaline process wastewater obtained from the one-stage or multistage scrubbing of the crude product from the nitration with aqueous alkaline solution such as sodium hydroxide solution, aqueous carbonate or hydrogencarbonate solution or aqueous ammonia solution has, depending on the base used, a pH of 7.5 to 13, preferably 8 to 10, measured at 60° C.

According to the invention, the alkaline process wastewater in step a) is adjusted by addition of acid to a pH below 5, preferably of 0.1 to 1. The pH figures are based in each case on the measurement at 60° C. Preference is given to acidifying using concentrated acid with an acid concentration of 70 to 95% by weight, particular preference to using sulfuric acid.

In a preferred embodiment of the invention, acidification in step a) is accomplished using sulfuric acid from the workup of the aqueous sulfuric acid-containing phase obtained in the nitration, more preferably the concentrated sulfuric acid. The concentrated sulfuric acid used for acidification has a concentration of 85 to 95% by weight, preferably of 90 to 93% by weight. In a preferred embodiment, only waste sulfuric acid obtained in the nitration is added for acidification in step a), particular preference being given to adding all of the waste sulfuric acid obtained in the nitration in step a). The addition of the concentrated sulfuric acid is advantageously controlled via online pH measurement.

According to the present invention it is preferred to acidify the alkaline process wastewater at temperature of 20 to 90° C., most preferred at temperatures of 55 to 70° C.

In the course of acidification of the alkaline process wastewater in step a), an organic phase separates out, which comprises hydroxynitroaromatics, nitrobenzoic acids and neutral nitro species, and $NO_x$ escapes from the aqueous acidic phase during and also after attainment of the target pH. In the case that the alkaline scrubbing liquid used was aqueous alkali metal carbonate or alkali metal hydrogencarbonate solution, large amounts of $CO_2$ additionally escape. The gaseous phase which separates out comprises, in the case of preceding DNT scrubbing with aqueous alkali metal carbonates or alkali metal hydrogencarbonate solution, typically 70 to 98.9% by volume of carbon dioxide and 1.1 to 30% by volume of nitrous gases (NO, $NO_2$, $N_2O$) or $NO_x$, respectively. The gas mixture which separates out preferably comprises 80 to 98% by volume of carbon dioxide and 2 to 20% by volume of nitrous gases or $NO_x$, respectively.

When the process wastewater comprises, instead of alkali metal carbonate or alkali metal hydrogencarbonate, one or more other bases which do not form any gaseous components after the acidification, the gaseous phase consists essentially of $NO_x$, typically 47 to 98% nitrogen monoxide, 1 to 47% nitrogen dioxide and 1 to 6% dinitrogen monoxide.

In a preferred embodiment, the $NO_x$ are stripped out of the acidic aqueous and organic phases by an inert gas, i.e. inert gas is passed through the two phases and entrains the $NO_x$ absorbed/dissolved therein. The inert gas is preferably selected from nitrogen, mixtures of nitrogen and oxygen, air and/or carbon dioxide.

In the process according to the invention, it has been found to be particularly advantageous when the alkaline process wastewater originates from the alkaline scrubbing with aqueous solutions of alkali metal carbonate and/or alkali metal hydrogencarbonate. The acidification of the process wastewater alkalized with these bases forms not only the gaseous $NO_x$ already described but also a large amount of gaseous $CO_2$, which simultaneously ensures stripping of $NO_x$ out of the acidic process wastewater. This embodiment is particularly advantageous because additional stripping with inert gas can be dispensed with.

In step b), the phase comprising $NO_x$ in gaseous form is removed, i.e. separated from the organic and acidic aqueous phases. This is preferably performed prior to the further treatment of the organic and aqueous phases.

After step b), the $NO_x$ present in the gaseous phase removed, in a preferred embodiment, is processed further to nitric acid in step c). The process according to the invention for workup of alkaline process wastewaters from the nitration of aromatic compounds to mono-, di- and trinitroaromatics comprises, in this embodiment, the following steps
a) acidifying the process wastewater by adding acid to a pH below 5, which forms an organic phase which separates out, an acidic aqueous phase and a gaseous $NO_x$-containing phase, and
b) removing the gaseous $NO_x$ containing phase,
c) further processing the $NO_x$ present in the gaseous phase removed in step b) to give nitric acid.

Preferably, the $NO_x$-containing phase removed in step b) is supplied in step c), without prior purification and removal of other gas constituents, directly to an absorption column for nitric acid production.

The nitric acid present in step c) is preferably recycled into the nitration of the aromatic compounds. In a particularly preferred embodiment of the process according to the invention, the $NO_x$-containing phase is fed into the absorption columns of the $NO_x$ absorption of the nitric acid recovery in the nitration plant. It is particularly advantageous when all of the $NO_x$-containing phase removed in step b) is recycled directly and without purification and prior removal of any $CO_2$ present.

The recycling is preferably effected to an absorber column, as installed for the workup of the $NO_x$ offgases from the sulfuric acid concentration, for example according to the process DE 10 143 800 C1. This produces, under a pressure of 6 bar, and temperatures of 10-60° C., from $NO_x$ with countercurrent flow of water, nitric acid with a concentration of about 60% by weight, which is subsequently available for the nitration of aromatic compounds and can be recycled in this way to the process for nitration. The $CO_2$ entrained is inert under the conditions which exist and can be removed via the top of the column.

After step b), the $NO_x$-containing phase removed can also be sent to further processes known to those skilled in the art for disposal of $NO_x$, for example to an incineration.

The aqueous and organic phases obtained in step a) can be worked up further. In one embodiment, the organic phase is removed and the acidic aqueous phase is extracted with a solvent. Preferred solvents are the aromatic compounds which are used as starting materials in the nitration.

In a further embodiment of the invention, after removal of the organic phase, the aqueous phase, optionally after extraction with an organic solvent, is sent to an ozonolysis, a thermolysis or a biological wastewater treatment.

The process according to the invention can be performed batchwise or continuously. Preference is given in accordance with the invention to performing the process continuously.

The process according to the invention is illustrated in detail hereinafter by examples:

Example 1

A 1000 mL stirred vessel with gas outlet, internal thermometer and pH electrode is initially charged with 500 mL of an alkaline process wastewater from scrubbing with aqueous sodium carbonate solution from the production of dinitrotoluene at 60° C. Subsequently, the entire interior is purged with nitrogen and completely inertized. The concentrations of carbonate and nitrite in the process wastewater are listed in Table 1. The pH of the alkaline process wastewater was 9. Subsequently, the process wastewater is admixed with 93% concentrated waste sulfuric acid until a pH of 1 is obtained and the mixture is stirred for 5 minutes. The gas mixture which arises is passed through the gas outlet into an adjacent absorber cascade, the first two bottles being filled with an exactly acidified 0.02 M potassium permanganate solution (for NO determination), and the last two bottles with a 0.1 M NaOH (for $CO_2$ determination). Subsequently, the dead volume of the apparatus was thoroughly purged (not stripped) with nitrogen in order to pass a maximum amount of gas formed into the absorber columns. Thereafter, the NaOH solutions were combined and the carbonate content was determined potentiometrically with 0.1 M HCl, and the amount of $CO_2$ is calculated in this manner. The potassium permanganate solutions were combined and then titrated with oxalic acid and the amount of nitrogen monoxide was determined. The gas volumes determined are shown in Table 1. The resulting gas volume (calculated from NO and $CO_2$) was 3.25 l.

TABLE 1

| Component | Wastewater mixture Starting values | Wastewater mixture After acidification | Gas composition | Gas volume |
|---|---|---|---|---|
| Carbonate | 1.60% | n.d.* | 86% by vol. of $CO_2$ | 2.795 l |
| Nitrite | 0.30% | n.d.* | 14% by vol. of NO | 0.455 l |

*not detectable (by ion chromatography)

Example 2

A 1000 mL stirred vessel with gas outlet, internal thermometer and pH electrode is initially charged with 500 mL of 1.0 M NaOH containing 0.3% $NaNO_2$ at 60° C. Subsequently, the entire interior is purged with nitrogen and completely inertized. Subsequently, the solution is admixed with 93% concentrated waste sulfuric acid until a pH of 1 is obtained and the mixture is stirred for 5 minutes. The gas mixture formed is passed through the gas outlet into an adjacent absorber cascade filled with an exactly acidified 0.02 M potassium permanganate solution. Subsequently, the dead volume of the apparatus was thoroughly purged (not stripped) with nitrogen in order to pass a maximum amount of gas formed into the absorber columns. Thereafter, the potassium permanganate solutions were combined and then titrated with oxalic acid, and the NO volume was determined.

Subsequently, the same experiment was conducted except that the purging of the apparatus with nitrogen was effected below the liquid level (stripping). Table 2 lists the results after purging with 50 l/h of nitrogen after 5 minutes in each case.

TABLE 2

NaOH/$NO_2$ mixture, influence of stripping

| Stripping | Starting values for nitrite | Gas volume formed (calculated from NO) |
|---|---|---|
| No | 0.30% | 0.260 l |
| Yes | 0.30% | 0.455 l |

The stripping (purging) of the acidified solution leads to a higher yield of NO driven out.

Compared to example 1, it is also found that the $CO_2$ which forms in the case of use of aqueous sodium hydrogencarbonate solution as an alkaline scrubbing liquid is an effective means of stripping.

Example 3

A 50 L stirred vessel with gas outlet, process wastewater inlet, acid feed, pH electrode and process wastewater outlet was continuously supplied with 220 l/h of alkaline process wastewater and continuously adjusted to a pH of 1 with waste sulfuric acid (93%). The acidified process wastewater was supplied constantly at about 220 l/h (regulated by fill level) to a further treatment (stirred cell extractor, pulsed column, mixer-settler). The gas mixture formed was supplied via a line to a compressor and finally to an absorber column which is installed for the workup of $NO_x$ offgases from the sulfuric acid concentration according to the process DE 101 43 800 C1.

Example 4

A 50 L stirred vessel with gas outlet, process wastewater inlet, acid feed, pH electrode and process wastewater outlet was continuously supplied with 220 l/h of alkaline process wastewater and continuously adjusted to a pH of 1 with waste sulfuric acid (93%). The acidified process wastewater was supplied constantly at about 220 l/h (regulated by fill level) to a further treatment (stirred cell extractor, pulsed column, mixer-settler). The gas mixture formed was supplied via a line and without further compression to an incineration furnace connected to a flue gas cleaning system.

The invention claimed is:

1. A process for workup of an alkaline process wastewater obtained from a nitration of an aromatic compound to produce mono-, di- and tri-nitroaromatics, comprising:
   (a) acidifying the alkaline process wastewater by adding acid to obtain a mixture with a pH below 5, which forms an organic phase which separates out, an acidic aqueous phase, and a gaseous $NO_x$-containing phase, and
   (b) removing the gaseous $NO_x$-containing phase,
   wherein the acid in (a) is a concentrated sulfuric acid obtained from the workup of an aqueous sulfuric acid-containing phase obtained in the nitration, wherein the concentrated sulfuric acid has a sulfuric acid concentration of 85% to 95% by weight.

2. The process of claim 1, wherein the $NO_x$ formed in the course of acidification in step (a) are stripped out of the organic and acidic aqueous phases by an inert gas and converted to the gaseous phase.

3. The process of claim 1, wherein the $NO_x$ formed in the course of acidification in (a) are stripped out of the organic and acidic aqueous phases by nitrogen, mixtures of nitrogen and oxygen, air or carbon dioxide and converted to the gaseous $NO_x$-containing phase.

4. The process of claim 1, wherein the alkaline process wastewater originates from the scrubbing of a crude product from the nitration with aqueous alkali metal carbonate or alkali metal hydrogencarbonate solution, and nitrogen oxides are stripped out of the organic and acidic aqueous phases by the carbon dioxide formed in the course of acidification of the alkaline process wastewater and converted to the gaseous $NO_x$-containing phase.

5. The process of claim 1, wherein the aromatic compound to be nitrated is benzene, toluene, xylene, chlorobenzene or dichlorobenzene.

6. The process of claim 1, wherein the alkaline process wastewater is acidified at a temperature of 20 to 90° C.

7. The process of claim 6, wherein the temperature is from 55 to 70° C.

8. The process of claim 1, wherein (b) is performed before further treatment of the organic and aqueous phases.

9. The process of claim 1, wherein the acidic aqueous phase is extracted with a solvent after removal of the organic phase.

10. The process of claim 1, wherein the acidic aqueous phase, after removal of the organic phase, is sent to an ozonolysis, a thermolysis or a biological wastewater treatment.

11. The process of claim 1, further comprising, after (b):
(c) further processing of the $NO_x$ present in the gaseous $NO_x$-containing phase removed to produce nitric acid.

12. The process of claim 11, wherein the gaseous $NO_x$-containing phase removed is supplied in (c), without prior purification and removal of other gas constituents, directly to an absorption column for nitric acid production.

13. The process of claim 11, wherein the nitric acid obtained in (c) is recycled into the nitration of the aromatic compounds.

14. The process of claim 1, wherein the $NO_x$-containing phase removed after (b) is sent to an incineration.

15. The process of claim 1, wherein the alkaline process wastewater contains nitrites and the amount of nitrites is lowered by 90% to 99% after (a) and (b).

16. The process of claim 1, wherein the concentrated sulfuric acid has a sulfuric acid concentration of 90% to 93% by weight.

17. In a process of nitrating an aromatic compound, wherein an alkaline process wastewater is obtained from the nitration and a concentrated sulfuric acid phase is obtained from a distillation of an aqueous phase produced in the nitration, the improvement comprising (a) acidifying the alkaline process wastewater with the concentrated sulfuric acid phase to produce an aqueous phase, an organic phase and a gaseous $NO_x$-containing phase and (b) removing the gaseous $NO_x$-containing phase.

\* \* \* \* \*